(12) United States Patent
Ter-Petrosyan et al.

(10) Patent No.: US 9,913,990 B2
(45) Date of Patent: *Mar. 13, 2018

(54) USE OF A DEDICATED REMOTE CONTROL AS AN INTERMEDIARY DEVICE TO COMMUNICATE WITH AN IMPLANTABLE MEDICAL DEVICE

(71) Applicant: Boston Scientific Neuromodulation Corporation, Valencia, CA (US)

(72) Inventors: Habet Ter-Petrosyan, Panorama City, CA (US); Gaurav Gupta, Valencia, CA (US); Sridhar Kothandaraman, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/396,748

(22) Filed: Jan. 2, 2017

(65) Prior Publication Data

US 2017/0106196 A1    Apr. 20, 2017

Related U.S. Application Data

(63) Continuation of application No. 14/789,564, filed on Jul. 1, 2015, now Pat. No. 9,533,162.

(60) Provisional application No. 62/108,908, filed on Jan. 28, 2015, provisional application No. 62/040,369, filed on Aug. 21, 2014.

(51) Int. Cl.
*A61N 1/372* (2006.01)

(52) U.S. Cl.
CPC ..... *A61N 1/37247* (2013.01); *A61N 1/37229* (2013.01)

(58) Field of Classification Search
None
See application file for complete search history.

(56) References Cited

U.S. PATENT DOCUMENTS

| 5,548,271 A | 8/1996 | Tsuchiyama et al. |
| 5,720,770 A | 2/1998 | Nappholz et al. |
| 5,759,199 A | 6/1998 | Snell et al. |

(Continued)

FOREIGN PATENT DOCUMENTS

WO    WO 2003/095024    11/2003

OTHER PUBLICATIONS

U.S. Appl. No. 61/789,700, filed Jun. 3, 2013, Kothandaraman.

(Continued)

*Primary Examiner* — Brian T Gedeon
(74) *Attorney, Agent, or Firm* — Lewis, Reese & Nesmith, PLLC (57) ABSTRACT

Systems and methods are disclosed in which an external device such as a consumer mobile device (e.g., smart phone) is used as an external controller to bi-directionally communicate with an Implantable Medical Device (IMD) using a dedicated patient remote control (RC) as an intermediary device to translate communications between the two. The dedicated RC contains a graphical user interface allowing for control and monitoring of the IMD even if the mobile device is not present in the system, which is useful as a back-up should the mobile device experience problems. Use of the dedicated RC as an intermediary device broadens the utility of other computing devices to operate as an external controller for an IMD even if the computing device and IMD do not have compliant communication means.

20 Claims, 8 Drawing Sheets

(56) References Cited

U.S. PATENT DOCUMENTS

| | | |
|---|---|---|
| 6,167,312 A | 12/2000 | Goedeke |
| 6,219,580 B1 | 4/2001 | Faltys et al. |
| 6,250,309 B1 | 6/2001 | Krichen et al. |
| 6,434,429 B1 | 8/2002 | Kraus et al. |
| 6,442,432 B2 | 8/2002 | Lee |
| 6,490,487 B1 | 12/2002 | Kraus et al. |
| 6,497,655 B1 | 12/2002 | Linberg et al. |
| 6,516,227 B1 | 2/2003 | Meadows et al. |
| 6,553,262 B1 | 4/2003 | Lang et al. |
| 6,574,509 B1 | 6/2003 | Kraus |
| 6,662,052 B1 | 12/2003 | Sarwal et al. |
| 6,738,671 B2 | 5/2004 | Christophersom et al. |
| 7,043,305 B2 | 5/2006 | Kenknight et al. |
| 7,060,030 B2 | 6/2006 | Von Arx et al. |
| 7,177,698 B2 | 2/2007 | Klosterman et al. |
| 7,191,012 B2 | 3/2007 | Boveja et al. |
| 7,313,529 B2 | 12/2007 | Thompson |
| 7,324,850 B2 | 1/2008 | Persen et al. |
| 7,369,897 B2 | 5/2008 | Boveja et al. |
| 7,475,245 B1 | 1/2009 | Healy et al. |
| 7,597,643 B2 | 10/2009 | Shimada |
| 7,742,821 B1 | 6/2010 | Vamos et al. |
| 7,848,819 B2 | 12/2010 | Goetz et al. |
| 7,865,242 B2 | 1/2011 | Diebold et al. |
| 7,885,712 B2 | 2/2011 | Goetz et al. |
| 7,911,397 B2 | 3/2011 | Degner et al. |
| 7,962,222 B2 | 6/2011 | He et al. |
| 7,978,062 B2 | 7/2011 | Lalonde et al. |
| 7,991,479 B2 | 8/2011 | Phillips et al. |
| 8,002,700 B2 | 8/2011 | Ferek-Petric et al. |
| 8,103,346 B2 | 1/2012 | Mass et al. |
| 8,126,731 B2 | 2/2012 | Dicks et al. |
| 8,130,093 B2 | 3/2012 | Mazar et al. |
| 8,140,160 B2 | 3/2012 | Pless et al. |
| 8,174,395 B2 | 5/2012 | Samuelsson et al. |
| 8,214,042 B2 | 7/2012 | Ozawa et al. |
| 8,265,757 B2 | 9/2012 | Mass et al. |
| 8,335,569 B2 | 12/2012 | Aghassian |
| 8,373,556 B2 | 2/2013 | LaLonde et al. |
| 8,395,498 B2 | 3/2013 | Gaskill et al. |
| 8,410,940 B2 | 4/2013 | Samuelsson et al. |
| 8,463,392 B2 | 6/2013 | Aghassian |
| 8,498,716 B2 | 7/2013 | Chen et al. |
| 8,543,208 B2 | 9/2013 | Pless et al. |
| 8,588,925 B2 | 11/2013 | Carbunaru et al. |
| 8,682,444 B2 | 3/2014 | Aghassian et al. |
| 8,983,615 B2 | 3/2015 | Tahmasian et al. |
| 2004/0088374 A1 | 5/2004 | Webb et al. |
| 2006/0142820 A1 | 6/2006 | Von Arx et al. |
| 2006/0212092 A1 | 9/2006 | Pless et al. |
| 2007/0073346 A1 | 3/2007 | Corbucci |
| 2008/0069869 A1 | 3/2008 | Rosenberg |
| 2008/0114416 A1 | 5/2008 | Theriot et al. |
| 2008/0208292 A1 | 8/2008 | Persen et al. |
| 2009/0024179 A1 | 1/2009 | Dronov |
| 2009/0063187 A1 | 3/2009 | Johnson et al. |
| 2009/0112281 A1 | 4/2009 | Miyazawa et al. |
| 2009/0210798 A1 | 8/2009 | Wu et al. |
| 2009/0292340 A1 | 11/2009 | Mass |
| 2010/0229324 A1 | 9/2010 | Conrad |
| 2010/0305663 A1 | 12/2010 | Aghassian |
| 2010/0318159 A1 | 12/2010 | Aghassian et al. |
| 2011/0071597 A1 | 3/2011 | Aghassian |
| 2011/0112611 A1 | 5/2011 | Aghassian |
| 2013/0007210 A1 | 1/2013 | Mass et al. |
| 2013/0073005 A1 | 3/2013 | Aghassian |
| 2013/0076535 A1 | 3/2013 | Sievert et al. |
| 2013/0079836 A1 | 3/2013 | Srivastava et al. |
| 2013/0215285 A1 | 8/2013 | Okuyanria et al. |
| 2014/0180366 A1 | 6/2014 | Edlund |
| 2014/0188193 A1 | 7/2014 | Vamos et al. |
| 2014/0354211 A1 | 12/2014 | Zottola et al. |
| 2015/0066110 A1 | 3/2015 | Tahmasian |
| 2015/0073498 A1 | 3/2015 | Kothandaraman |
| 2015/0073500 A1 | 3/2015 | Kothandaraman et al. |
| 2015/0231402 A1 | 8/2015 | Aghassian |
| 2015/0360038 A1 | 12/2015 | Zottola et al. |

OTHER PUBLICATIONS

Kothandaraman, Sridhar, "Replaceable RF Communications Card for Implantable Medical Device Programmers", Prior Art Database Technical Disclosure, pp. 1-4 (Jul. 3, 2003).

Energy Micro, EFM® 32, Connect the EFM32 with a Smart Phone through the Audio Jack, Rev.1.03 (May 2013).

Supersonic IQ-209 FM transmitter, Spec Sheet (date unknown).

Naztech N3030 Universal FM Transmitter, Spec Sheet (date unknown).

International Search Report and Written Opinion regarding corresponding PCT Application No. PCT/US2015/039003, dated Sep. 15, 2015.

USE OF A DEDICATED REMOTE CONTROL AS AN INTERMEDIARY DEVICE TO COMMUNICATE WITH AN IMPLANTABLE MEDICAL DEVICE

CROSS-REFERENCE TO RELATED APPLICATIONS

This application is a continuation of U.S. Non-Provisional application Ser. No. 14/789,564, filed Jul. 1, 2015 (now U.S. Pat. No. 9,533,162), which is a non-provisional of U.S. Provisional Patent Application Ser. Nos. 62/108,908, filed Jan. 28, 2015, and 62/040,369, filed Aug. 21, 2014. Priority is claimed to these applications, and they are incorporated herein by reference in their entireties.

FIELD OF THE INVENTION

The present invention relates generally to implantable medical device systems, and more particularly to external systems and methods for communicating with an implantable medical device.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators (DBS) to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any Implantable Medical Device (IMD) or in any IMD system.

Figure 1:
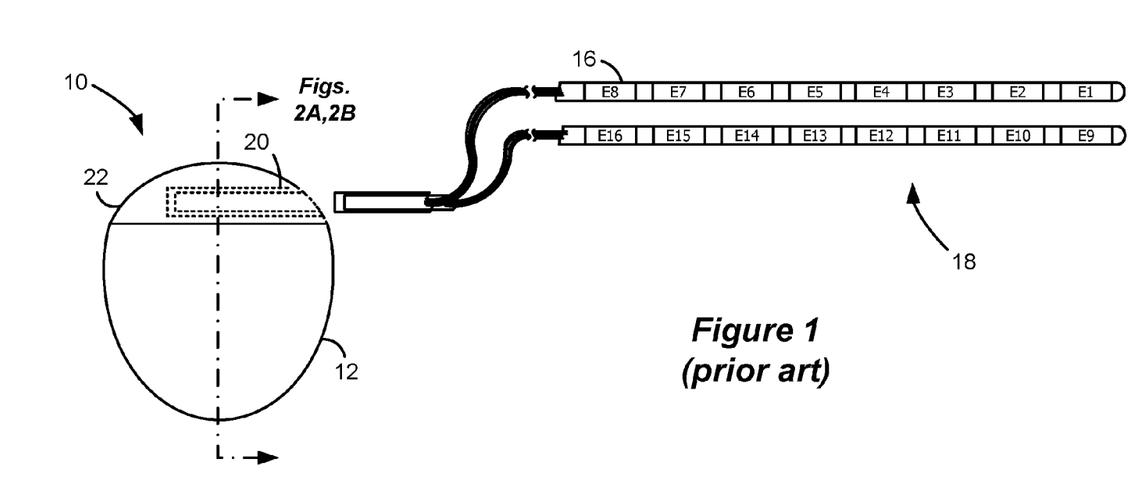
FIG. 1 shows an Implantable Medical Device (IMD) in accordance with the prior art.

As shown in FIG. 1, a SCS system includes an Implantable Pulse Generator (IPG) 10 (hereinafter, and more generically, IMD 10), which includes a biocompatible device case 12 formed of titanium for example. The case 12 typically holds the circuitry and battery 14 necessary for the IMD 10 to function. The IMD 10 is coupled to electrodes 16 via one or more electrode leads 18 (two of which are shown). The proximal ends of the leads 18 are coupled to the IMD 10 at one or more lead connectors 20 fixed in a header 22, which can comprise an epoxy for example. In the illustrated embodiment, there are sixteen electrodes, although the number of leads and electrodes is application specific and therefore can vary. In an SCS application, two electrode leads 18 are typically implanted on the right and left side of the dura within the patient's spinal column. The proximal ends of the leads 18 are then tunneled through the patient's flesh to a distant location, such as the buttocks, where the IMD case 12 is implanted, at which point they are coupled to the lead connectors 20.

Figure 2A:
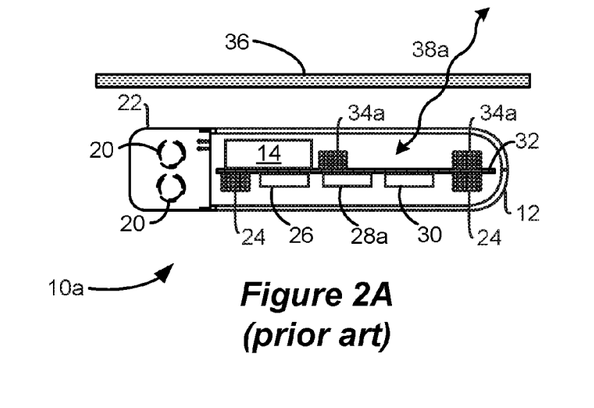
FIGS. 2A and 2B respectively show cross sections of an IMD having a coil telemetry antenna and an RF telemetry antenna, in accordance with the prior art.
Figure 2B:
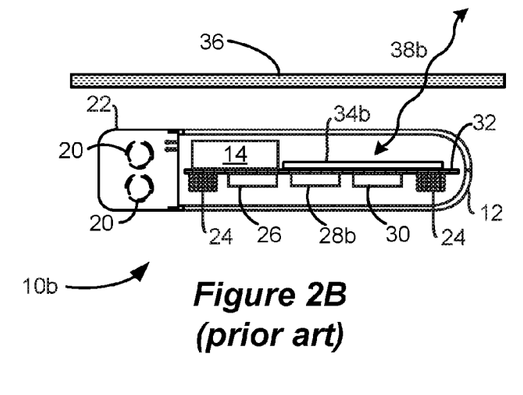

Cross sections of two examples of IMD 10, 10a and 10b, are shown in FIGS. 2A and 2B. Both contain a charging coil 24 for wirelessly charging the IMD's battery 14 using an external charging device (not shown). (If battery 14 is not rechargeable, charging coil 26 can be dispensed with). Both IMDs 10a and 10b also contain control circuitry such as a microcontroller 26, telemetry circuitry 28 (discussed further below), and various components 30 necessary for IMD operation, such as stimulation circuitry for forming therapeutic pulses at the electrodes 16. The charging coil 24, battery 14, microcontroller 26, telemetry circuitry 28, and other components 30 are electrically coupled to a printed circuit board (PCB) 32.

Different in the two IMDs 10a and 10b are the telemetry antennas 34a and 34b used to transcutaneously communicate data through the patient's tissue 36 with devices external to the patient (not shown in FIGS. 2A and 2B). In IMD 10a (FIG. 2A), the antenna comprises a coil 34a, which can bi-directionally communicate with an external device along a magnetic induction communication link 38a, which comprises a magnetic field of typically less than 10 MHz operable in its near-field to communicate at a distance of 12 inches or less for example. Telemetry circuitry 28a is electrically coupled to the coil antenna 34a to enable it to communicate via magnetic induction link 38a, and generally includes driver circuitry for energizing the coil antenna 34a to transmit data and amplifier/filter circuitry for resolving data received at the coil 34. Telemetry circuitry 28a generally also operates in accordance with a modulation scheme (defining how data to be transmitted is modulated on the link 38a and will be demodulated when received) and a communication protocol (defining the manner in which the data is formatted). Telemetry circuitry 28a receives the data to be transmitted in digital form from the microcontroller 26, and provides received digital data to the microcontroller 26 for interpretation. A typical modulation scheme used by telemetry circuitry 28a is Frequency Shift Keying (FSK), although other modulation schemes could also be used. In FIG. 2A, the external device would also contain communication means (e.g., a coil antenna; telemetry circuitry) compatible with the magnetic induction link 38a and the protocol used by the IMD 10a, as explained subsequently.

In IMD 10b (FIG. 2B), short-range Radio Frequency (RF) communication means—including short-range RF antenna 34b and compliant short-range RF telemetry circuitry 28b—are provided that operate in accordance with a short-range RF communication standard and its underlying protocols to bi-directionally communicate with an external device along a short-range RF communication link 38b. Short-range RF communication link 38b typically operates using far-field electromagnetic waves ranging from 10 MHz to 10 GHz or so, and allows communications between devices at distances of about 50 feet or less. Short-range RF standards supported by short-range RF telemetry circuitry 28b and antenna 34b include, for example, Bluetooth, BLE, NFC, Zigbee, WiFi (802.11x), and the Medical Implant Communication Service (MICS). Short-range RF antenna 34b can take any number of well-known forms for an electromagnetic antenna, such as patches, slots, wires, etc., and can operate as a dipole or a monopole. The external device in FIG. 2B would also contain short-range RF communication means compatible with short-range RF link 38b and the standard/protocols used in IMD 10b, as explained subsequently.

Although both of antennas 34a and 34b in IMDs 10a and 10b are shown in FIGS. 2A and 2B inside of case 12, they may also be placed within the IMD's header 22, or on the outside of the case 12. Although shown as exclusive in FIGS. 2A and 2B, an IMD 10 may have both of the different types of antennas 10a and 10b.

Different configurations for external devices used to communicate with IMDs such as 10a and 10b exist in the prior art. Such external devices are typically used to send or adjust the therapy settings the IMD 10a or 10b will provide to the patient (such as which electrodes 16 are active to issue pulses; whether such electrodes sink or source current (i.e., polarity); the duration, frequency, and amplitude of pulses, etc.), which settings together comprise a stimulation program for the patient. External devices can also act as receivers of data from the IMD 10*a* or 10*b*, such as various data reporting on the IMD's status and the level of the IMD's battery 14.

Figure 3:
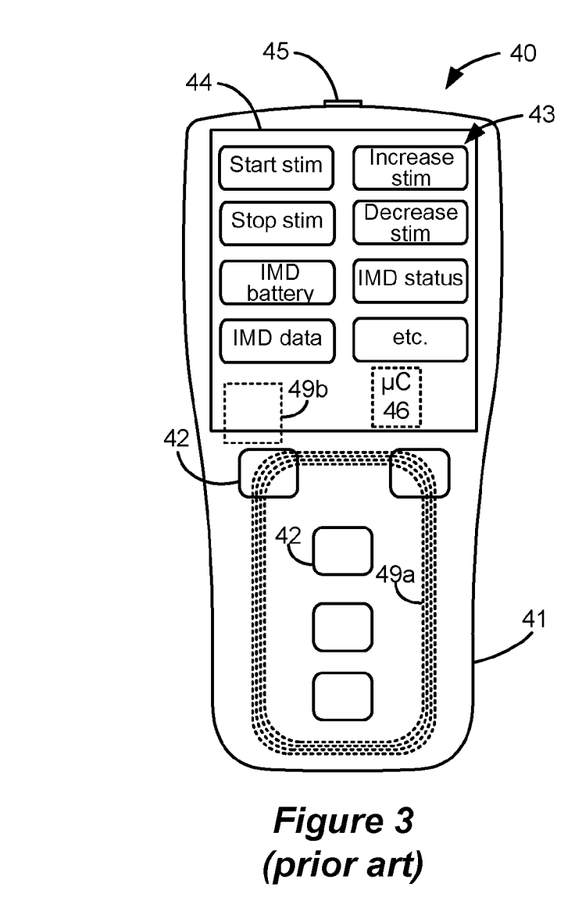
FIG. 3 show a dedicated remote control (RC) for communicating with an IMD, in accordance with the prior art.

An external device having such functionality is shown in FIG. 3 in the form of a patient remote control 40. Remote control (RC) 40 is typically hand-held, portable, and powered by a battery (not shown) within the RC's housing 41, which battery may be a primary battery or rechargeable. The RC 40 includes a Graphical User Interface (GUI) 43 similar to that used for a cell phone, including buttons 42 and a screen 44, and may have other interface aspects as well, such as a speaker. The RC 40 also includes within its housing 41 communication means, including a coil antenna 49*a* and/or a short-range RF antenna 49*b*, compatible with the link(s) 38*a* and/or 38*b* and the communication means in the IMDs 10*a* and/or 10*b*. Processing in the RC 40 is controlled via a microcontroller 46. As described above with respect to the IMDs 10*a* and 10*b*, antennas 49*a* and 49*b* would be associated with telemetry circuitry, although this is not shown in FIG. 3. One or more orthogonal coil antennas 49*a* driven out of phase could be used in RC 40 as well to improve communication coupling with the IMD 10*a* along magnetic induction link 38*a*, as discussed in U.S. Patent Application Publication 2009/0069869, with which the reader is assumed familiar.

Shown on the screen 44 in FIG. 3 are various options provided by the GUI 43 and selectable by a patient to control his IMD 10 (e.g. the stimulation program it is executing) or to monitor his IMD 10. Just a few typical options are depicted for simplicity that enable the patient to: start or stop stimulation; increase or decrease the amplitude of the stimulation pulses; check IMD monitoring information, such as the battery 14 level, operating status of the IMD, or other data telemetered from the IMD; etc.

Also shown in FIG. 3, and as disclosed in U.S. Pat. Nos. 8,498,716 and 8,588,925 which are incorporated herein by reference, an RC 40 can includes a port 45 on its housing 41, which may comprise a USB port for example. The '716 patent teaches that USB port 45 can be used to: recharge the RC 40's battery from a wall plug (assuming such battery is rechargeable); exchange data with another external device (such as an external computer; not shown); or couple to an external charging coil (not shown) to charge the IMD's battery 14 (assuming such battery 14 is rechargeable), in effect allowing RC 40 to operate as a combination RC/charger.

The '925 patent teaches that USB port 45 can be used to convey contraindication information—e.g., activities that might be counter-indicated for an IMD patient such as Magnetic Resonance Imaging (MRI) or some physical activity—to a person of interest, such as the patient or her clinician. In this regard, the '925 patent teaches that a cable can couple between port 45 on the RC 40 and a port on an external computer to allow contraindication information to be reviewed outside of the RC 40 itself Alternatively, the '925 patent teaches that a memory stick (not shown) may be coupled to port 45 to allow contraindication information resident in the RC 40 to be written to the memory stick, which memory stick can then be removed from the RC 40 and coupled to the external computer where the contraindication information can be reviewed.

External devices such as the RC 40 of FIG. 3 were historically built by the manufacturer of the IMDs, and thus were generally dedicated to communicate only with such IMDs. As such, dedicated RC 40 is not freely programmable by a patient, but is instead limited to the IMD functionality provided by the manufacturer. (However, the microcode operating in the RC's microcontroller 46 may be upgraded from time to time in manners specified by the manufacturer). However, there are many user-programmable commercial mobile devices, such as cell phones, that can provide GUIs and have inherent communication means suitable for functioning as a wireless external controller for an IMD.

Figure 4A:
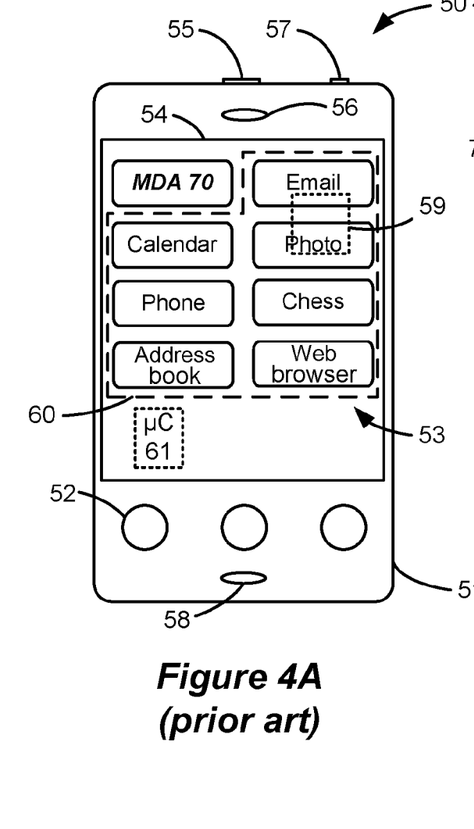
FIG. 4A shows a graphical user interface (GUI) of a mobile device.
Figure 4B:
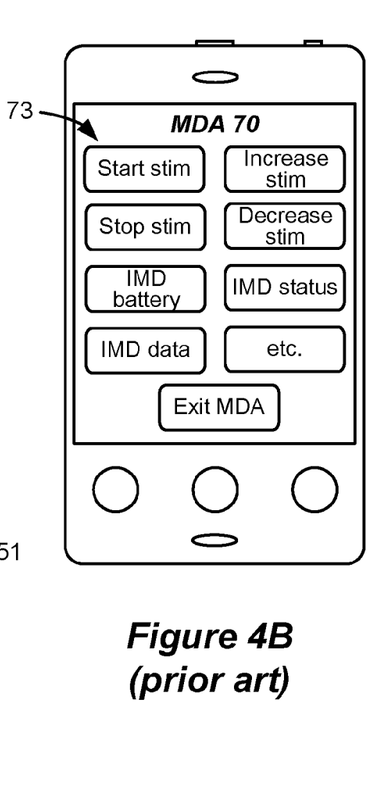
FIG. 4B shows a GUI of a Medical Device Application (MDA) on the mobile device for communicating with an IMD, in accordance with the prior art.

FIGS. 4A and 4B show an example of a mobile device 50 configured for use as an external controller for an IMD, as described in commonly-owned U.S. Patent Application Publications 2015/0073498 and 2015/0231402, which are incorporated herein by reference. The mobile device 50 may be a commercial, multipurpose, consumer device, such as a cell phone, tablet, personal data assistant, laptop or notebook computer, or like device—essentially any mobile, handholdable device capable of functioning as a wireless external controller for an IMD. Examples include the Apple iPhone or iPad, Microsoft Surface, Nokia Lumia devices, Samsung Galaxy devices, and Google Android devices for example.

As shown in FIG. 4A, the mobile device 50 includes a GUI 53 with a screen 54, which may also receive input if it is a touch screen. The mobile device 50 may also have buttons 52 (e.g., a keyboard) for receiving input from the patient, a speaker 56, and a microphone 58. Mobile device 50 further includes a battery within its housing 51, although not shown, which battery may be a primary battery or rechargeable. Mobile device 50 can also include ports 55 and 57, which are subsequently explained. Mobile device 50 further includes at least one short-range RF antenna 59, again as subsequently explained, and would include telemetry circuitry compliant with that antenna(s), although not shown. Processing in the mobile device 50 is controlled by a microcontroller 61.

Shown on the screen 54 is a typical home screen GUI 53 provided by the mobile device 50 when first booted or reset. A number of applications ("apps") 60 may be present and displayed as icons on the mobile device home screen GUI 53, which the patient can select and execute.

One of the applications (icons) displayed in FIG. 4A is a Medical Device Application (MDA) 70, which may reside as microcode in the mobile device 50's microcontroller 61. When MDA 70 is executed by the patient, the microcontroller 61 will configure the mobile device 50 for use as an external controller to communicate with an IMD. FIG. 4B shows the GUI 73 provided by the MDA 70 after it is executed, which includes options selectable by a patient to control his stimulation program or monitor his IMD, similar to what was described earlier with respect to the GUI 43 of the dedicated RC 40 of FIG. 3.

The MDA 70, like other applications 60 selectable in the mobile device 50, may have been downloaded using traditional techniques, such as from an Internet server or an "app store." Although not strictly necessary, MDA 70 is logically developed and provided by the manufacturer of the IMD, and may be made available in different versions to work with different mobile device operating systems (e.g., iOS, Android, Windows, etc.). One skilled in the art will understand that MDA 70 comprises instructions that can be stored in the mobile device 50 or on an Internet server for example on non-transistory machine-readable media, such as magnetic, optical, or solid-state discs, integrated circuits, memory sticks, tapes, etc.

When the MDA 70 on the mobile device 50 is first selected and executed, or when an appropriate selection is made in the MDA, wireless communications with the IMD can be established using a communication means in the mobile device 50 and enabled by the MDA 70. The above-incorporated '498 Publication discloses different examples in which such communication can occur, illustrated here in FIGS. 5A-5C.

Figure 5A:
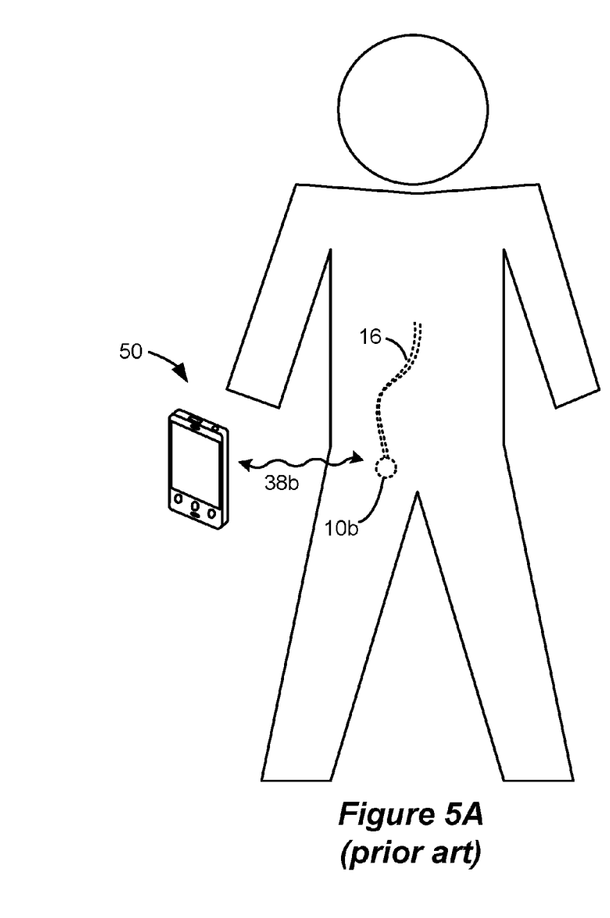
FIGS. 5A-5C show different manners in which a mobile device can wirelessly communicate with an IMD using the MDA of FIG. 4B, in accordance with the prior art.

In FIG. 5A, the MDA 70 establishes wireless communication directly with the IMD10b along short-range RF link 38b using short-range RF communication means supported by the mobile device 50 (e.g., WiFi or Bluetooth), including one of its short-range RF antennas 59 (FIG. 4A). In this instance, the IMD 10b would include short-range communication means compatible with short-range RF link 38b such as a short-range RF antenna 34b shown earlier with respect to FIG. 2B.

Figure 5B:
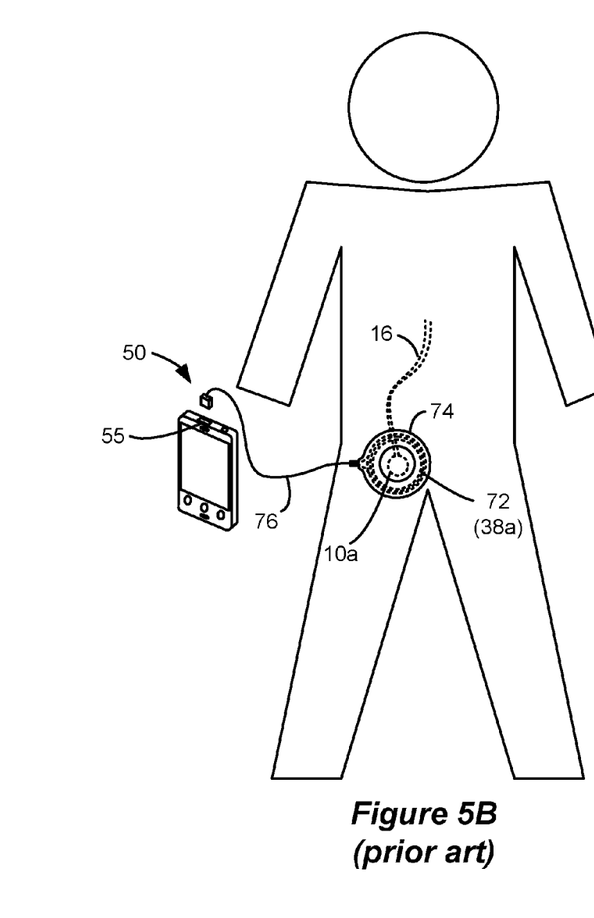

In FIG. 5B, a coil antenna 72 in a communication head 74 is coupled by a cable 76 to the port 55 on the mobile device 50, such as a USB port. In this example, the coil antenna 72 can be placed proximate to the IMD 10a to establish a magnetic induction link 38a, perhaps as modulated via FSK as mentioned earlier. The IMD 10a would include communication means compatible with magnetic induction link 38a such as a coil antenna 34a shown earlier with respect to FIG. 2A. The MDA 70 in this example would cause the mobile device 50 to issue and receive data at its USB port 55, which data may be modulated or digital depending whether the modulation/demodulation circuitry resides in the mobile device 50 or the communication head 74.

Figure 5C:
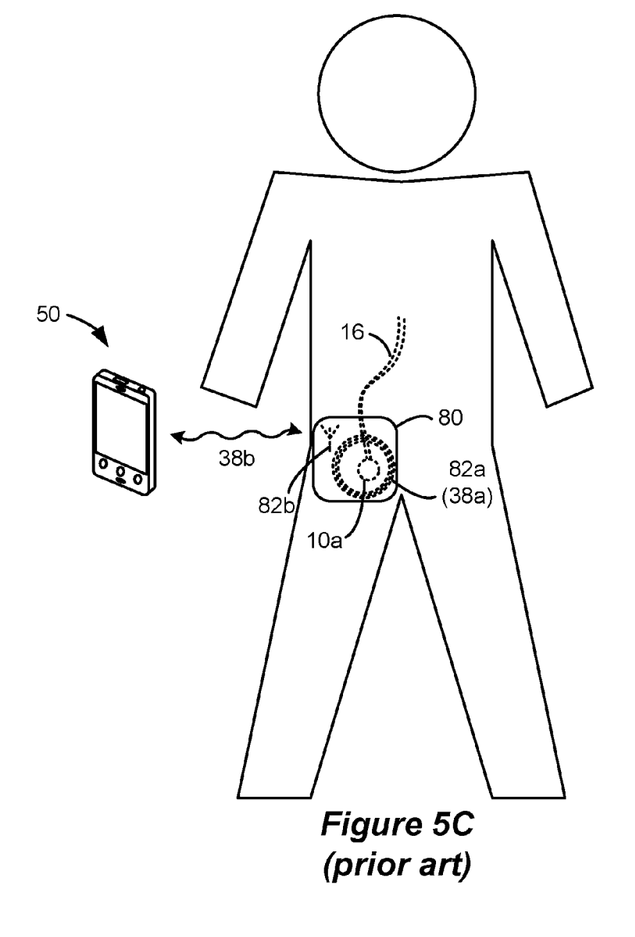

In FIG. 5C, the mobile device 50 communicates with the IMD 10a via an intermediary bridge 80. The bridge 80 contains first communication means including a short-range RF antenna 82b for wirelessly communicating with the mobile device 50 via short-range RF link 38b, and second communication means including a coil antenna 82a for wirelessly communicating with the IMD 10a via a magnetic induction link 38a. The bridge 80, which is preferably battery powered (battery not shown), essentially "translates" data on short-range RF link 38b into (FSK) data on magnetic induction link 38a, and vice versa. The MDA 70 can thus program the mobile device 50 to use its inherent short-range RF communication means (e.g., short-range antenna 59) to communicate with the IMD 10a, even if the IMD 10a is not compatible with such means, because the bridge 80 can translate and communicate with both. The communication system of FIG. 5C is further explained in U.S. Patent Application Publication 2013/0215285, which is incorporated herein by reference.

The '498 Publication further teaches that the MDA 70 can secure the mobile device 50 by controlling hardware and software that could affect, or worse corrupt, its use as an IMD external controller. Addressing such security issues is prudent because general-purpose commercial mobile devices by virtue of their broad connectivity are potentially subject to software viruses or tampering ("hacking"). For example, the '498 Publication discloses that the MDA 70 upon execution can temporarily configure the mobile device 50 to prevent operation inconsistent with external controller functionality, such as by disabling or reconfiguring hardware modules in the mobile device 50 that are either unnecessary or could potentially interfere with operation of the MDA 70. The MDA 70 can also terminate or temporarily suspend software tasks that might interfere with secure operation of the mobile device 50 as an external controller, such as other apps 60 displayable and executable from the mobile device home screen GUI 53 (FIG. 4A), or other software tasks that may run in the background of the mobile device in manners not immediately noticeable to the patient.

Figure 6A:
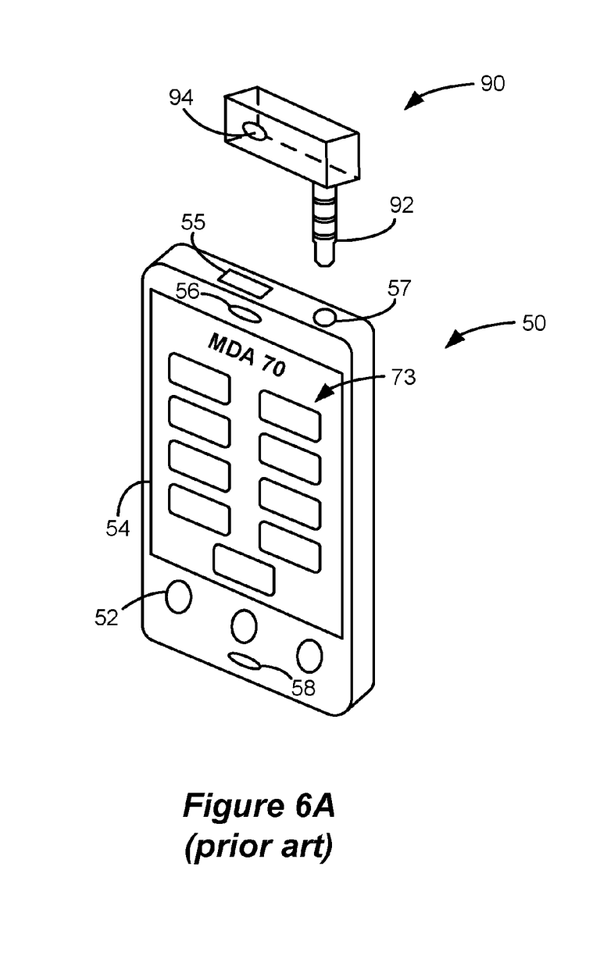
FIGS. 6A-6C show various plug-in accessories to configure a mobile device to operate as an external controller for an IMD, in accordance with the prior art.
Figure 6B:
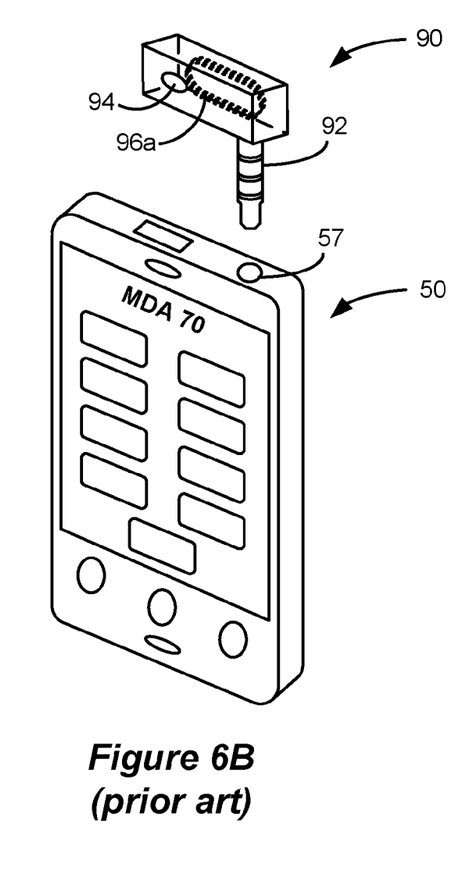
Figure 6C:
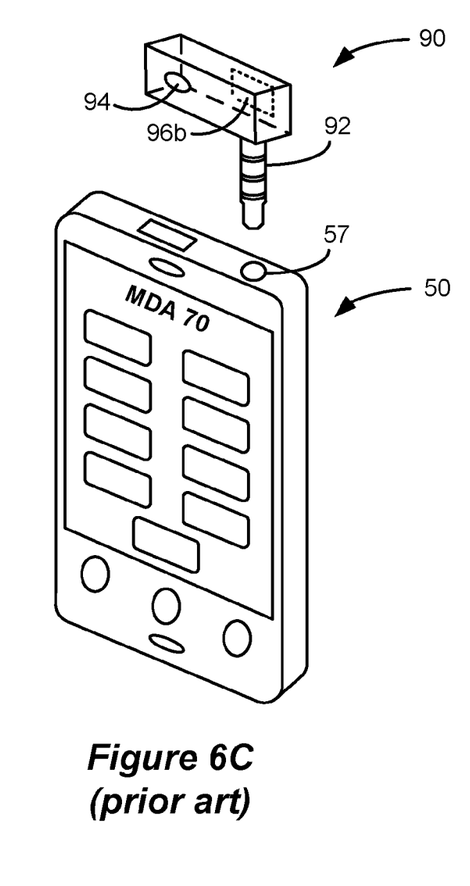

The above-incorporated '402 Publication describes other techniques for using a mobile device 50 to communicate with an IMD 10a or 10b, which are illustrated here in FIGS. 6A-6C. In these techniques, an accessory 90 with a connector 92 is coupled to an audio port 57 on the mobile device. The connector 92 and audio port 57 are co-axial, and typically comprise a left and right audio output signal, an audio input signal (MIC), and a ground. Typically a pair of headphones and/or a microphone (not shown) can be coupled to the audio port 57 on the mobile device 50 as is well known. Such signaling allows the accessory 90 to communicate bi-directionally with the mobile device 50. Additionally, the accessory 90 can receive power from the mobile device 50 for its circuitry via connector 92/audio port 57, or can include its own battery, as explained in the '402 Publication. Although not depicted here, the '402 Publication teaches that the accessory 90 can be coupled to a different type of port on the mobile device 50, such as the USB port 55.

In the '402 Publication, the accessory 90 is used to facilitate quick execution of the MDA 70 on the mobile device 50, essentially allowing a user instant access to GUI 73 to communicate with his IMD 10. In one example, the accessory 90 is used to immediately execute the MDA 70 on the mobile device, either upon pressing a switch 94 and/or when the accessory 90 is inserted into the audio port 57 and automatically validated by the mobile device 50. The accessory 90 can facilitate immediate execution of the MDA 70 by by-passing security measures inherent in the mobile device 50, such as screen locks or passwords, thus removing these encumbrances. The accessory 90 can further enable securing of the mobile device 50 for use as an IMD external controller, as explained above with respect to the '498 Publication. The use of the accessory 90 also provides a physical measure of IMD security, as the MDA 70 can be programmed to not execute if the patient's accessory 90 is not present and validated. Electronics in the accessory 90 are described in the '402 Publication but are largely omitted here.

In the example of FIG. 6A, once the MDA 70 is executed, communication with the IMD occurs using short-range communication means provided in the mobile device 50 itself, including at least one of its short-range RF antennas 59. This assumes use with an IMD (e.g., 10b) having a short-range RF antenna (e.g., 34b) compliant with the communication standard used by antenna 59.

If the IMD is not so compliant, other examples in the '402 Publication provide antennas in the accessories 90, as shown in FIGS. 6B and 6C. In FIG. 6B, the accessory 90 includes a coil antenna 96a capable of communicating with an IMD compliant with such communication means, such as IMD 10a of FIG. 2A. In FIG. 6C, the accessory 90 includes a short-range RF antenna 96b compliant with the IMD, such as IMD 10b of FIG. 2B. In this example, the accessory 90's short-range RF antenna 96b can communicate using a standard supported by the IMD 10b (e.g., MICS) which may not be supported by the short-range RF antenna 59 in the mobile device 50 (e.g., WiFi or Bluetooth). In either of the examples of FIGS. 6B and 6C, communications with the IMD 10a or 10b as controlled by the MDA 70 on the mobile device 50 occurs bi-directionally using the accessory 90's antennas 96a or 96b and the data path provided by audio port 57/connector 92. As such, the mobile device 50 in this example is only used for its easy provision of a GUI, rather than for its inherent communication capabilities (such as its non-compliant short-range RF antenna 59). Otherwise, the accessories 90 of FIGS. 6B and 6C provide the same benefits to security and ease of use provided by the accessory 90 of FIG. 6A.

DETAILED DESCRIPTION

While the prior art techniques described in the Background provide workable manners for communicating with an IMD that are advantageous in leveraging the programmable and communicative aspects inherent in commercial mobile devices, the inventors see room for improvement.

In particular, the inventors recognize that while mobile devices 50 can substitute for dedicated external IMD controllers 40 provided by the manufacturer, perhaps as assisted by supporting software and hardware discussed previously (such as MDA 70, FIGS. 4A and 4B; communication head 74, FIG. 5B; bridge 80, FIG. 5C; or plug-in accessories 90, FIGS. 6A-6B), it may still be prudent for manufacturer to provide a dedicated RC 40 to the IMD patient, such as shown in FIG. 3.

Providing a dedicated RC 40 to IMD patients is prudent at least to act as a "back up" to allow IMD communications should the mobile device 50 experience problems. While a manufacturer can provide and guarantee a MDA 70 and supporting hardware to enable a mobile device 50 to function as an external controller, the manufacturer cannot guarantee the reliability and operation of the mobile device itself, let alone all of the various mobile devices its patients may wish to use to communicate with their IMDs. General-purpose mobile devices 50 also present security issues that should generally not be inherent in dedicated RCs 40, as discussed in the Background with reference to the '498 Publication.

Additionally, a manufacturer cannot assume that a patient will have a mobile device 50 operable to communicate with an IMD. A given patient may simply not own a mobile device 50, or her device 50 may not be suitable for IMD communications—for example, if it is too old, or if its operating system is otherwise not compliant with the IMD manufacturer's requirements (such as the manufacturer's MDA 70). Or, a given patient's mobile device 50 may not have the inherent capability of communicating with the patient's IMD, at least directly. As discussed in the Background, a patient's mobile device 50 may inherently have short-range RF communication means such as antenna 59 (operating per Bluetooth or WiFi communication standards) that may not be compatible with the communication means provided in an IMD—such as a magnetic induction coil antenna 34a in the IMD 10a of FIG. 2A, or a short-RF MICS antenna 34b in the IMD 10b of FIG. 2B. As discussed in the Background, supporting hardware may be necessary to allow communications between incompatible mobile devices 50 and IMDs 10 (e.g., communication head 74, bridge 80, plug-in accessories 90, etc.), which again the manufacturer cannot assume the patient will have at their disposal.

In short, sole reliance on mobile devices 50 as external IMD controllers may be problematic. As a result, IMD manufacturers may still wish to additionally provide dedicated external IMD controllers 40 to their IMD patients to ensure a reliable and safe means to allow IMD therapy to be adjusted, monitored, or even turned off if necessary.

Thus, a patient may have two means available to communicate with his IMD 10—a dedicated RC 40 and a mobile device 50. The inventors have discerned that these devices 40 and 50 can function together in a manner easing use of the mobile device 50 to operate as an external controller by allowing the patient's dedicated RC 40 to act as an intermediary bridge to couple communication from the mobile device 50 to the patient's IMD 10. This is similar in functionality to the bridge device 80 discussed in the Background with reference to FIG. 5C, and as disclosed in the above-referenced '285 Publication. However, unlike the bridge 80, the dedicated RC 40 includes a full user graphical user interface (GUI) 43 (including screen 44 and buttons 42) which allows the patient to control therapy settings the IMD and to monitor data transmitted from the IMD. Bridge 80, by contrast, merely contains communication means to in effect translate communications to and from the IMD 10. Bridge 80 contains no user interface, let alone a graphical user interface, to allow IMD control or monitoring.

Figure 7:
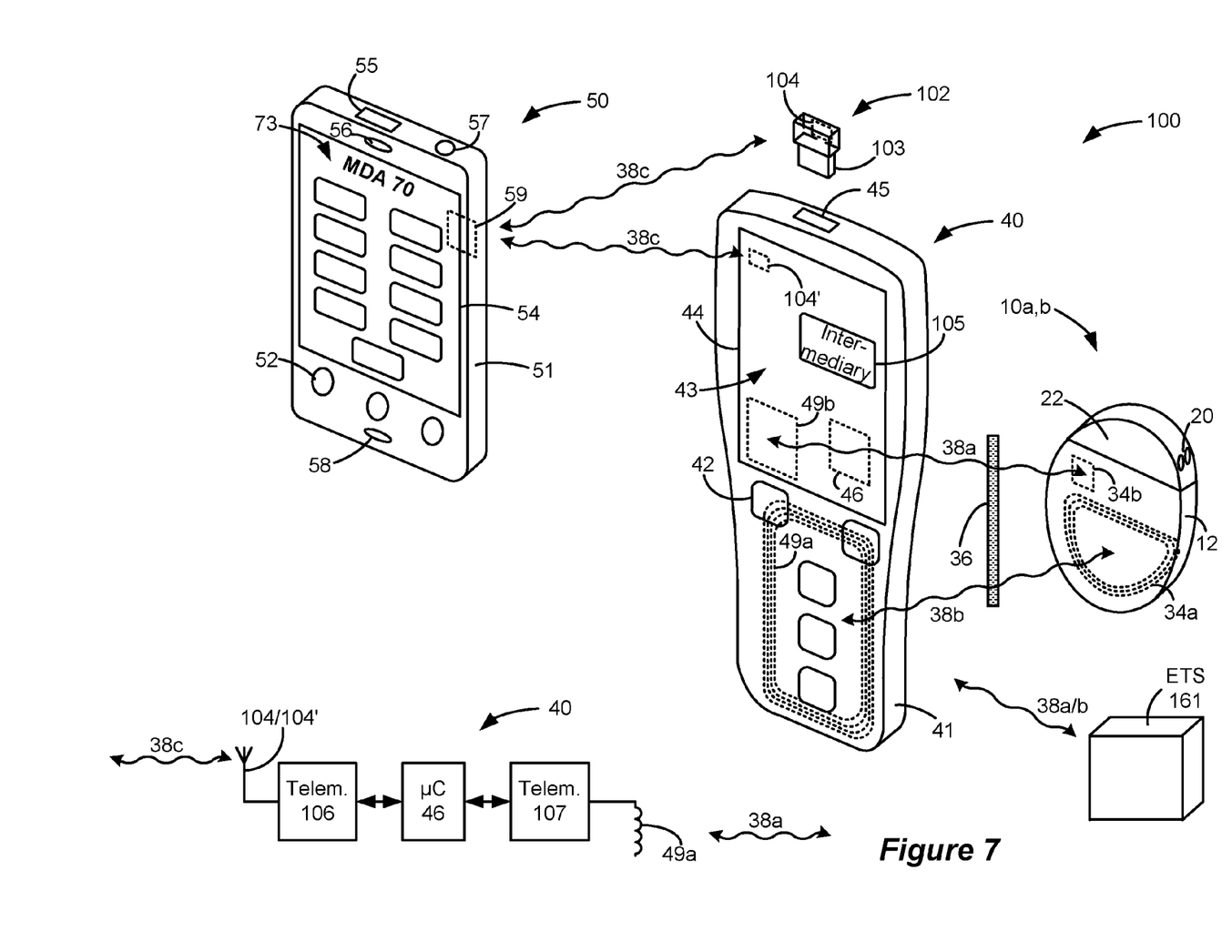
FIG. 7 shows an improved system in which a dedicated RC (FIG. 3) is used as an intermediary device to translate communication between a mobile device and an IMD, in accordance with an example of the invention.

FIG. 7 shows an example of a system 100 in which a mobile device 50 uses a dedicated RC 40 to communicate with an IMD 10. The mobile device 50 as before can be programmed with an MDA 70 to allow IMD control and monitoring of IMD information via GUI 73, and which may perform additional security related tasks befitting mobile device 50 use as an external controller, as discussed earlier. Also shown is one of the mobile device 50's inherent antennas 59 and (associated telemetry circuitry not shown), which is internal to the mobile device's housing 51. Antenna 59 as explained earlier is preferably a short-range RF antenna operable with communication means typically inherent in mobile device 50, such as those operable according to Bluetooth and WiFi standards.

The dedicated RC 40 in system 100 has been modified to include a short-range RF antenna 104 which is compliant with the short-range RF communication means (e.g., antenna 59) in the mobile device 50, thus enabling bi-directional communications between the mobile device 50 and the dedicated RC 40 via a short-range RF link 38*c*. The GUI 43 provided by the dedicated RC 40 may be identical to the GUI 73 rendered by the MDA 70 at the mobile device 50, or at least may include identical functionality in terms of selectable options useable to control and monitor the IMD 10. Alternatively, the GUIs 73 and 43 of the devices 50 and 40 may comprise a subset of the functionality provided by the other device 40 or 50.

Different versions of short-range RF antennas can be used in the dedicated RC 40. An external short-range antenna 104 is shown in FIG. 7 as contained within a dongle 102 coupleable to a port on the dedicated RC 40's housing 41. In the example shown, a connector 103 on the dongle 102 is coupleable to the dedicated RC 40's USB port 45. Such RF-compliant dongles 102 are well known and need not be specially manufactured for use with the dedicated RC. For example, suitable dongles 102 coupleable to USB ports can include those used by a wireless computer mouse (input device) to communicate with a computer. As one skilled in the art will understand, dongle 102 may contain other control circuitry (not shown) as necessary to supplement operation of the short-range RF antenna 104.

Use of an external short-range antenna 104 is beneficial as it allows the type of short-range RF antenna to be readily changed to match the standard being used by the short-range RF antenna 59 in the mobile device 50. For example, one dongle 102 may include a Bluetooth antenna 104, while another may include a WiFi antenna 104, etc. Short-range antenna 104' by contrast is contained within dedicated RC 40's housing 41. As the antenna 104' is internal and not accessible, care should be taken to ensure that the antenna 104' will be compliant with communication standard used in a majority of mobile devices 50 (e.g., Bluetooth).

Communications between the dedicated RC 40 and the IMD 10 occurs using the antenna 49*a/b* used for communications with the IMD 10 even when the mobile device 50 is not present. As explained in the Background, the type of antenna 49 used can be dictated by the type of antenna 34 used in the IMD 10. If the IMD 10*a* includes a coil antenna 34*a* (FIG. 2A), the dedicated RC 40 would likewise include a coil antenna 49*a* for bi-directional communication along a magnetic induction link 38*a*. If the IMD 10*b* includes a short-range RF antenna 34*b* (FIG. 2B), the dedicated RC 40 would likewise include a short-range RF antenna 49*b* for bi-directional communication along a short-range RF link 38*b*. In this case, care should be taken to ensure that the antennas 49*b* and 34*b* are compliant with the same short-range RF communication standard (e.g., MICS). Preferably, and as is typical, the antenna 49*a/b* is internal to the housing 41 of the dedicated RC 40.

Regardless of the particular antennas and links used, the dedicated RC 40 acts as an intermediary device to permit bi-directional communication between the mobile device 50 and the IMD 10, regardless of the communication means supported by those two devices. In this regard, the microcontroller 46 in the dedicated RC 40 can operate to translate between different communication formats (i.e., different standards, different modulation schemes, different protocols, etc.) used by the mobile device 50 and the IMD 10.

Assume for example that the MDA 70 operating on the mobile device 50 enables the mobile device's Bluetooth short-range RF antenna 59 to transmit and receive communications to and from the IMD 10, and that the IMD has a coil antenna 34*a* (FIG. 2A). In this circumstance, the dedicated RC 40 will have a Bluetooth short-range RF antenna 104/104' compliant with the communication means in the mobile device 50, and a coil antenna 49*a* compliant with the communication means in the IMD 10*a*, as shown in the schematic at the bottom of FIG. 7. Also shown in the schematic are telemetry circuitries 106 and 107 coupled to and between each of the antennas 104/104' and 49*a* and the RC's microcontroller 46. The telemetry circuitries 106 and 107 generally include modulation/antenna driver circuitry for transmitting data and amplifier/filter/demodulation circuitry for receiving data in accordance with the format of the data on the links they support. Each of the telemetry circuitries 106 and 107 communicated digital data bi-directionally with the microcontroller.

The microcontroller 46 in the dedicated RC 40 can be programmed to translate data received in one format and to transmit that data in a second format. For example, when antenna 104/104' receives Bluetooth formatted data from short-range antenna 59 in the mobile device 59 via short-range RF link 38*c* (such as a control instruction for the IMD to increase or decrease stimulation, etc.), the microcontroller 46 can cause FSK telemetry circuitry 107 to transmit that data in an FSK format from its coil antenna 49*a* via magnetic induction link 38*a* to the coil antenna 34*a* in the IMD 10*a*, allowing the IMD 10*a* to then execute the control instruction. Likewise, the dedicated RC 40 can receive monitoring information transmitted from the coil antenna 34*a* in the IMD 10*a* via magnetic induction link 38*a* at its coil antenna 49*a*, and its microcontroller 46 can cause Bluetooth telemetry circuitry 106 to transmit that data in a Bluetooth format from its short-range RF antenna 104/104' via short-range RF link 38*c* to the short-range antenna 59 in the mobile device 50, where such received data can be viewed using the MDA GUI 73.

When so operating as an intermediary, the dedicated RC 40 may enter an intermediary mode of operation in which the dedicated RC 40 only operates to translate between the mobile device 50 and IMD 10. Such an intermediary mode can be separate and distinct from a normal operating mode in which the dedicated RC 40's GUI 43 is active to receive user inputs to control and monitor the IMD. In other words, the GUI 43 of the dedicated RC 40 may be disabled during the intermediary mode to prevent use of the dedicated RC 40 to control and monitor the IMD 10. Alternatively, the dedicated RC 40 can enable intermediary translating functionality between the mobile device 50 and the IMD 10 even during a normal operating mode in which IMD control and monitoring functions are still accessible from the dedicated RC 40's GUI 43.

Entering the intermediary operation mode, or otherwise enabling intermediary translating functionality, can be enabled in the dedicated RC 40 in any number of ways. For example, if the dedicated RC 40's short-range RF antenna 104 is external (e.g., in dongle 102), the dedicated RC 40 can enable translating of data when it senses that the dongle 102 has been inserted into an appropriate port (e.g., 45) on the dedicated RC 40. Alternatively, translating of data can comprise an option 105 selectable by a user on the GUI 43 of the dedicated RC 40, as shown in FIG. 7. In another alternative, the dedicated RC 40 will always translate data received at one antenna 49*a/b* or 104/104' and translate and retransmit that data at the other antenna 104/104' or 49*a/b*, even if there is no device (mobile device 50 or IMD 10) in proximity to receive the translated data, in which case needless transmission of the translated data will be harmless.

Note in the system of FIG. 7 that the dedicated RC 40, as well as providing its own GUI 43 permitting control and monitoring of the IMD 10, supplants supporting hardware otherwise used in the prior art to alleviate incompatibilities between the communication means used in the mobile device 50 and the IMD 10. For example, communication head 74 (FIG. 5B) and plug-in accessories 90 (FIGS. 6A-6B) are not required to be used with the mobile device 50.

When the system of FIG. 7 is used, and in particular when the IMD 10a has a coil antenna 34a (FIG. 2A), it is preferable to place the dedicated RC 40 in proximity to the IMD 10a because the magnetic induction link 38a supported by coil antenna 34a in the IMD 10a between them is relatively short (e.g., 12 inches or less as noted earlier). Assuring dedicated RC-to-IMD 10a proximity can occur in any number of ways, depending on where the IMD 10 is implanted in the body. For example, if the IMD is a Spinal Cord Stimulation (SCS) IPG 10, it would be implanted in the upper buttocks. If it is a Deep Brain Stimulator (DBS) IPG 10, it would be implanted under the collar bone in the patient's chest. Various belts or holsters into which the dedicated RC 40 can be inserted can be used hold the dedicated RC 40 in place and proximate to the IMD. Alternatively, a cord can be attached to the dedicated RC 40 to suspend it from the neck or waist in good proximity to the IMD 10a. The dedicated RC 40 could also include fastening means attached to its housing 41 to allow it to be attached to the patient's clothing, such as a clip for example. Dedicated RC-to-IMD proximity is less important if the IMD 10b has a short-range RF antenna 34b (FIG. 2B) operable at longer distances.

Figure 8:
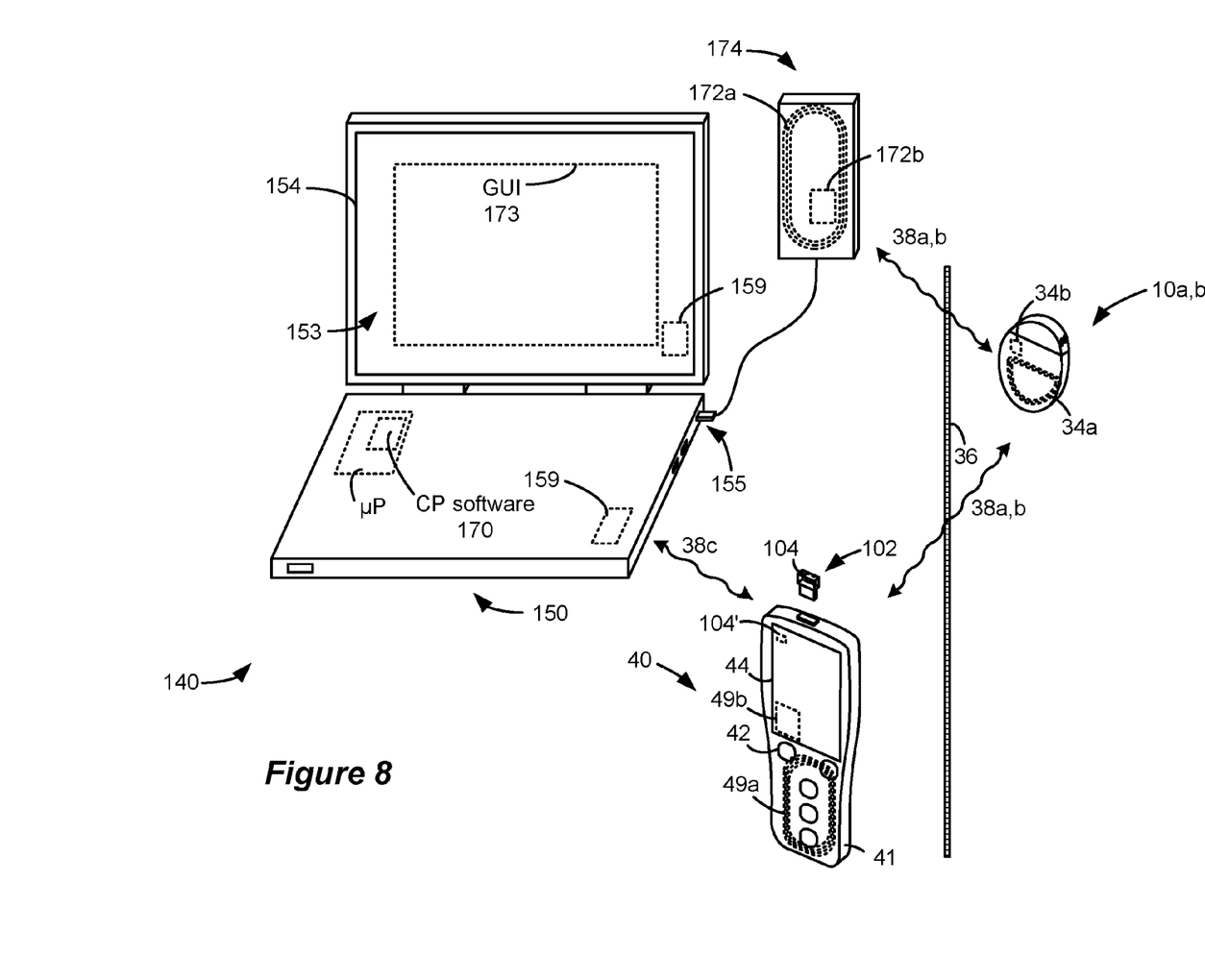
FIG. 8 shows use of the dedicated RC as described in FIG. 7 as an intermediary in a clinician programmer system, thus obviating the need for a wand in such system, in accordance with an example of the invention.

It should be noted that devices and systems other than a mobile device 50 can benefit from use of the dedicated RC 40 as an intermediary to communicate with an IMD. For example, FIG. 8 shows use of the dedicated RC 40 as an intermediary device in the context of a clinician programmer (CP) system 140 such as is described in U.S. Patent Application Publication 2015/0360038, which is incorporated herein by reference. CP system 140 is typically used by a clinician to set up operation of a patient's IMD after implantation and to determine optimal stimulation programs for a patient. In contrast to a mobile device 50, a CP system 140 is generally stationary and located at an office of the clinician.

As shown, CP system 140 comprises a computing device 150, such as a desktop, laptop, or notebook computer, a tablet, a mobile smart phone, a Personal Data Assistant (PDA)—type mobile computing device, etc. (hereinafter "CP computer"). In FIG. 8, CP computer 150 is shown as a laptop computer that includes a typical computer GUI 153 such as a screen 154, a mouse, a keyboard, speakers, a stylus, a printer, etc., not all of which are shown for convenience.

As explained further in the '038 Publication, CP software 170 operable in the CP computer 150 is used to render a GUI 173 on the screen 154 of the CP computer 150 to allow for control and monitoring of the IMD 10, in addition to many other more-complicated functions of significance to the clinician but not normally accessible by the patient via a mobile device 50 (MDA 70) or a dedicated RC 40. In this respect, CP computer 150 and CP software 170 are analogous to the mobile device 50 and MDA 70 described earlier.

In the example shown in FIG. 8, the antenna used in the CP system 140 to communicate with the IPG 10 includes a wand 174 which is somewhat analogous to the communication head 74 described earlier for use with mobile device 50 (FIG. 5B) in that it includes a coil antenna 72 for bi-directionally communicating with an IMD 10a having a coil antenna 34a (FIG. 2A), and is coupleable to a (USB) port 155 on the CP computer 150. Wand 174 may also include a short-range RF antenna 172b compliant with an IMD 10b having a short-range RF antenna 34b (FIG. 2B). (Wand 174 in an actual CP system would likely contain only one of antennas 172a or 172b depending on the nature of the IMD 10 supported).

Use of the dedicated RC 40 as an intermediary device disposes of the need for a wand 174 in the CP system 140, even if the CP computer 150 and the IMD 10 cannot otherwise directly communicate. Instead, a patient can bring his dedicated RC 40 to his clinician's office when the CP system 140 will be used. During IPG communications, the CP system 140 can instead use communication means inherent in the CP computer 150, such as one or more of its internal short-range RF antennas 159, which may be located in various places in the CP computer 150. The dedicated RC 40 can receive data via short-range RF link 38c from the antenna 159 at antenna 104/104', translate such data into a proper format, and transmit it to the IMD 10 via one of its antennas 49a/b (depending on the nature of the IMD 10a/b). Transmission of data in the other direction from the IMD 10 to the CP computer 150 would likewise flow through the dedicated RC 40 as an intermediary. In short, use of the dedicated RC 40 obviates the need for a separate wand 174 coupleable to the CP computer 150 in the CP system 140.

Figure 9:
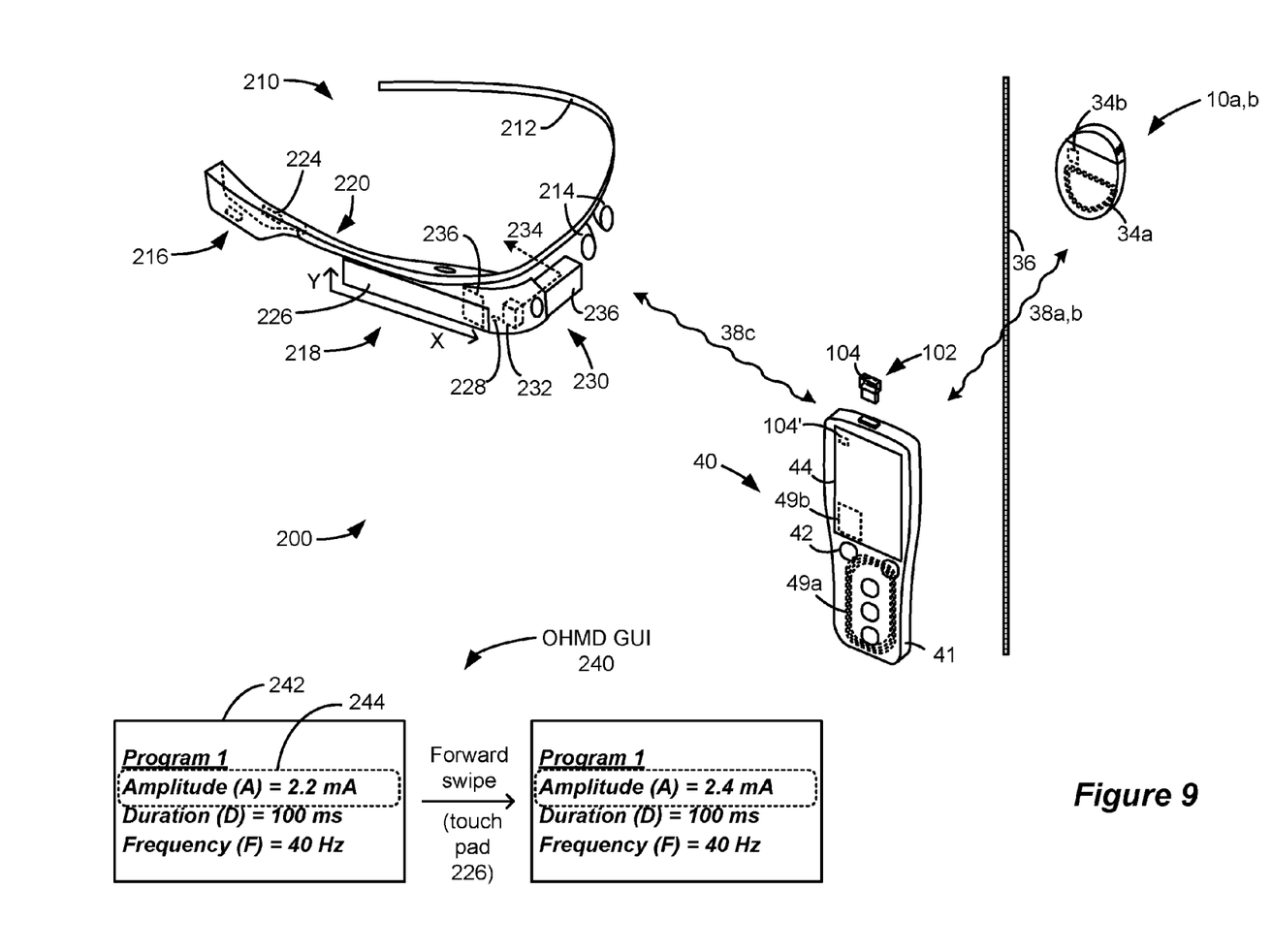
FIG. 9 shows use of the dedicated RC as described in FIG. 7 as an intermediary in a system in which an Optical Head-Mounted Display (OHMD) is used as the mobile device to control and monitor the IMD, accordance with an example of the invention.

FIG. 9 shows another example of a system 200 in which a dedicated RC 40 is used as an intermediary to pass communications between a mobile device and an IMD 10. However, in this example, the mobile device comprises a wearable mobile device 210, more specifically an Optical Head-Mounted Display 210, which is also disclosed in the above-referenced '038 Publication. OHMD 210 can in one example comprise the Google Glass™ OHMD, developed by Google, Inc. of Mountain View, Calif.

As described in the '038 Publication, OHMD 210 is configured to be wearable much like a pair of standard eyeglasses, and includes a frame 212 which also serves as the temples supported by the wearer's ears, and nose pads 214. Lenses (e.g., corrective or sunglasses lenses) may be affixed to the frame 212, but are not shown in FIG. 9. OHMD 210 may also be worn in conjunction with a wearer's normal eyeglasses.

Plastic affixed to the frame 212 generally defines a rearward housing 216 and a forward housing 218 on the OHMD 210's right temple. Plastic also defines a pass-through portion 220, which as well as defining a space for the wearer's right ear, also provides for the passing of wires between the two housings 216 and 218. The rearward housing 216 holds a rechargeable battery (not shown). A bone-conduction audio transducer 224 in the rearward housing 216 protrudes through the plastic and presses over the right ear to permit the wearer to hear sounds provided by the OHMD's GUI, which is explained below. OHMD 210 could also include a more-traditional audio speaker as well.

The forward housing 218 includes a printed circuit board (not shown), which supports the OHMD 210's main electronics, such as its microprocessor, and movement sensors providing input to a motion detector module in the electronics, including a three-axis accelerometer and a three-axis gyroscope. Also included in the forward housing 218 is a touch sensor (not shown), which allows the outer surface of the forward housing to operate as a touch pad 226. The touch pad 226 is sensitive to the wearer's touch across the two-dimensional expanse (X and Y) of the outer surface of the foreword housing 218, and can additionally be pressed ("tapped") similar to a button. The underside of the forward housing 218 additionally includes a microphone 228 for the receipt of voice input in addition to inputs receivable by the touch pad 226. The electronics of the OHMD 210 will include a voice detection module for interpretation of spoken voice inputs, as is well known.

The forward housing 218 also includes a display portion 230 of the OHMD 210, including an LED array 232 powered by the OHMD's microprocessor. Images 234 created at the LED array 232 are directed to a prism 236 containing a polarizing beam-splitter that direct the images 234 to the wearer's right eye. In this manner, the user is able to perceive the images 234 generated by the OHMD 210 and output by the display portion 230, which images 234 are provided slightly to the right of the wearer's center of vision, thus allowing the wearer to see the real world and the images on the display portion 230 simultaneously.

OHMD 210 in this example further includes bi-directional short-range RF communication means, which like the mobile device 50 described earlier preferably includes one or more antennas 236 and telemetry circuitry (not shown) compliant with Bluetooth and Wi-Fi communication standards. The antenna 236 is shown located in the forward housing 218, but could be present elsewhere, such as in the rearward housing 218.

As explained in the '038 Publication, the OHMD 210 can generate a Graphical User Interface (GUI) 240 using the display portion 230 that can be used to control and monitor the IMD 10. The input interface of the GUI 240 comprises one or more of the touch pad 226, the voice detection module (coupled to microphone 228), and the motion detector module coupled to the accelerometers and gyroscopes. This input interface allows a patient to navigate the GUI 240 to control and monitor his IMD 10 either by touch, voice, or head movements. Audio aspects (e.g., transducer 224 or another speaker) can also comprise part of the OHMD GUI 240.

The '038 Publication explains the OHMD GUI 240 in detail, and only a simple example is shown in FIG. 9. As seen by the patient via the display portion 230, a card 242 of information regarding a patient's current stimulation program (Program 1) is shown, including stimulation (pulse) amplitude, duration and, frequency. A cursor 244 highlights selection of a current parameter (amplitude in this example), which cursor can be moved using the input interface (i.e., by touch, voice, or movement). In the example shown, the patient increases the currently-selected stimulation amplitude by swiping forward on the touch pad 226, which then updates the information on the displayed card 242 (in this case reflecting an amplitude increase from 2.2 mA to 2.4 mA).

When adjustments in IMD control are made in this fashion, a control instruction is transmitted from the short-range RF antenna 236 in the OHMD 210 to the compliant short-range RF antenna 104/104' in the dedicated RC 40, where it is translated as explained earlier, and broadcast to the IMD 10 via its internal antenna 49a/b (depending on the nature of the IMD 10a/b). Although not depicted, the patient can also interact with the OHMD GUI 240 to retrieve monitoring information from the IMD 10. When this request is received at the IMD 10, the IMD 10 will in turn transmit the requested information from antenna 34a/b to antenna 49a/b in the dedicated RC 40, where it is translated and transmitted from short-range RF antenna 104/104' to short-range antenna 236 the OHMD 210, and rendered for user review via the OHMD GUI 240. As discussed earlier, use of the dedicated RC 40 as an intermediary between the OHMD 210 and the IMD 10 is particularly useful if the OHMD 210 and IMD cannot directly communicate given incompatibilities in their communication means.

It should be noted that antennas (e.g., 59, 159, or 236) in the various external IMD controllers (mobile device 50, CP computer 150, or OHMD 210) and antenna 104/104' associated with the dedicated RC 40 need not be short-range RF antennas, but could comprise other antennas for communicating by other means. For example, such antennas can operate in accordance with optical or acoustic principles as well, with the dedicated RC 40 still operating to translate communications with the IMD 10. Such RF antennas also need not comprise "short range" antennas, but could comprising longer-range RF antennas.

Microcontroller control circuitry operable in the IMD 10, RC 40, or in the various disclosed external controller devices (50, 150, 210) can comprise for example Part Number MSP430, manufactured by Texas Instruments, which is described in data sheets at http://www.ti.com/lsds/ti/microcontroller/16-bit_msp430/overview.page?DCMP=MCU_other&HQS=msp430, which is incorporated herein by reference. However, other types of control circuitry may be used in lieu of a microcontroller as well, such as microprocessors, FPGAs, DSPs, or combinations of these, etc.

Although particular embodiments have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A remote control for communicating with an Implantable Medical Device (IMD), comprising:
    a user interface and a first coil antenna, wherein the user interface is configured to enable a user to communicate data with the IMD via the first coil antenna in a first format via a first wireless link;
    a second short-range RF antenna configured to communicate data with an external device in a second format via a second wireless link;
    a housing, wherein the first coil antenna is within the housing; and
    control circuitry coupled to the first and second antennas, wherein the control circuitry is configured to translate data received at one of the first or second antenna in the first or second format into the other of the first or second format, and to transmit the translated data from the other of the first or second antenna.

2. The remote control of claim 1, wherein the first wireless link comprises a magnetic induction link, and the second wireless link comprises a short-range RF link.

3. The remote control of claim 1, further comprising a port on the housing, wherein the second short-range RF antenna is coupleable to the port outside of the housing.

4. The remote control of claim 3, wherein the second short-range RF antenna is contained within a dongle coupleable to the port.

5. The remote control of claim 1, wherein the port comprises a USB port.

6. A system for communicating with an Implantable Medical Device (IMD), comprising:
    a Medical Device Application (MDA) executable on an external device, wherein the MDA is configured to provide a second user interface to enable a user to transmit a second control instruction for the IMD via a second wireless link; and a remote control, comprising:
- a first user interface and a first antenna, wherein the first user interface is configured to enable a user to transmit a first control instruction for the IMD from the first antenna to the IMD via a first wireless link; and
- a second antenna configured to receive the second control instruction via the second wireless link,
- wherein the remote control is configured to translate the second control instruction and to transmit the translated second control instruction from the first antenna to the IMD via the first wireless link.

7. The system of claim 6, further comprising the external device, wherein the MDA is stored on the external device.

8. The system of claim 7, wherein the external device comprises a mobile device.

9. The system of claim 8, wherein the mobile device comprises a cell phone.

10. The system of claim 8, wherein the mobile device is wearable.

11. The system of claim 10, wherein the wearable mobile device comprises an Optical Head Mounted Display (OHMD).

12. The system of claim 6, wherein the first wireless link carries data in a first format, and wherein the second wireless link carries data in a second format.

13. The system of claim 6, wherein the first wireless link comprises a magnetic induction link, and the second wireless link comprises a short-range RF link.

14. The system of claim 6, wherein the first and second wireless links comprise short-range RF links.

15. The system of claim 6, wherein the remote control further comprises a housing, wherein the first and second antennas are within the housing.

16. The system of claim 6, wherein the remote control further comprises a housing, wherein the first antenna is within the housing, and wherein the second antenna is coupleable to a port on the housing.

17. The system of claim 16, wherein the second antenna is contained within a dongle coupleable to the port.

18. The system of claim 16, wherein the port comprises a USB port.

19. The system of claim 6, wherein the second antenna is removable from the remote control.

20. The system of claim 6, wherein the remote control is further configured to:
- receive first monitoring information from the IMD at the first antenna via the first wireless link, wherein the first user interface is configured to display the first monitoring information to the user; and
- receive second monitoring information from the IMD at the first antenna via the first wireless link; translate the second monitoring information; and transmit the translated second monitoring information from the second antenna to the external device via the second wireless link.

* * * * *